(12) United States Patent
Nakamura et al.

(10) Patent No.: US 8,270,073 B2
(45) Date of Patent: Sep. 18, 2012

(54) SURGICAL MICROSCOPE SYSTEM

(75) Inventors: Katsushige Nakamura, Tokyo (JP);
Masao Doi, Tokyo (JP); Masakazu Nakamura, Tokyo (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 818 days.

(21) Appl. No.: 12/052,897

(22) Filed: Mar. 21, 2008

(65) Prior Publication Data

US 2008/0231948 A1 Sep. 25, 2008

(30) Foreign Application Priority Data

Mar. 23, 2007 (JP) ................ 2007-077616

(51) Int. Cl.
*G02B 21/00* (2006.01)

(52) U.S. Cl. ..................................... 359/384

(58) Field of Classification Search .............. 359/368, 359/384
See application file for complete search history.

(56) References Cited

U.S. PATENT DOCUMENTS

| | | | |
|---|---|---|---|
| 5,528,417 A | 6/1996 | Nakamura | |
| 5,713,545 A * | 2/1998 | Nakamura | 248/123.2 |
| 6,050,530 A * | 4/2000 | Nakamura | 248/123.2 |
| 6,525,878 B1 | 2/2003 | Takahashi | |
| 2001/0038489 A1 | 11/2001 | Nakamura et al. | |
| 2004/0036962 A1* | 2/2004 | Brunner et al. | 359/368 |
| 2004/0090668 A1* | 5/2004 | Muller et al. | 359/368 |
| 2005/0154431 A1 | 7/2005 | Quistgaard et al. | |
| 2005/0247831 A1 | 11/2005 | Nakamura | |
| 2006/0232855 A1 | 10/2006 | Nakamura et al. | |
| 2008/0037113 A1 | 2/2008 | Nakamura | |

FOREIGN PATENT DOCUMENTS

| | | |
|---|---|---|
| EP | 1152275 | 11/2001 |
| EP | 1591817 | 11/2005 |
| JP | 9-070406 | 3/1997 |
| JP | 11-244301 | 9/1999 |
| JP | 2001-117049 | 4/2001 |
| JP | 2006-102155 | 4/2006 |
| WO | 01/45627 | 6/2001 |

OTHER PUBLICATIONS

English language Abstract of JP 11-244301.
Japan Office action, dated Apr. 26, 2011 along with an english translation thereof.

* cited by examiner

*Primary Examiner* — Frank Font
(74) *Attorney, Agent, or Firm* — Greenblum & Bernstein P.L.C.

(57) ABSTRACT

A surgical microscope system is disclosed. The surgical microscope is comprised of a stand which is comprised of a movable base and a support capable of free motion with keeping a particular orientation relative to the movable base; a stereoscopic surgical microscope linked with the support, which is comprised of a pair of first optical systems so as to provide a first stereoscopic magnified view; and a stereoscopic display device having a movable link with the stand, which is comprised of a display screen for displaying stereoscopic image taken by the first optical systems and a pair of second optical systems as to show the stereoscopic image as a second stereoscopic magnified view.

9 Claims, 8 Drawing Sheets

SURGICAL MICROSCOPE SYSTEM

CROSS-REFERENCE TO RELATED APPLICATIONS

This application claims priorities from Japanese Patent Application No. 2007-077616 filed on Mar. 23, 2007; the entire contents of which are incorporated herein by reference.

BACKGROUND OF THE INVENTION

1. Field of the Invention

The present invention relates to a surgical microscope system which shows stereoscopic magnified views of an objective body part through both a main optical system and a sub-system.

2. Description of the Related Art

Some surgeries such as brain surgeries require operations performed by microscopy. For such uses, surgical microscopes having very long focal distances are usually used. Japanese Patent Application Laid-open No. H11-244301 discloses a related art in which a surgical microscope provides a stereoscopic magnified view of an objective body part for a surgeon and another eyepiece provides a monocular magnified view for an assistant (or a trainee of the operation, or such). In accordance with this related art, the assistant is merely allowed to observe the monocular view and cannot observe a stereoscopic view in common with, and further simultaneously with, the surgeon. Moreover the eyepiece for the assistant accompanies movement of the surgical microscope when the surgeon moves the surgical microscope for the purpose of changing views.

SUMMARY OF THE INVENTION

The present invention is intended for providing a surgical microscope system which provides stereoscopic magnified views of an objective body part for both a main person and an assistant person simultaneously and independently.

In accordance with an aspect of the present invention, a surgical microscope system is comprised of a stand including a movable base and a support capable of free motion with keeping a particular orientation relative to the base, a stereoscopic surgical microscope linked with the support, the microscope including a pair of first optical systems so as to provide a first stereoscopic magnified view; and a stereoscopic display device having a movable link with the stand, the display device including a display screen configured to display stereoscopic image taken by the first optical systems and a pair of second optical systems so as to show the stereoscopic image as a second stereoscopic magnified view.

Preferably, the surgical microscope system is further comprised of a camera optically coupled with the first optical systems and electronically coupled with the display screen so as to project the stereoscopic image onto the display screen. More preferably, the camera is comprised of a pair of imagers respectively optically coupled with the first optical systems to take the stereoscopic image. Still more preferably, the display screen is comprised of a pair of separate screens respectively electronically coupled with the imagers.

Still preferably, the surgical microscope system is further comprised of a subsidiary arm linked with the support and the stereoscopic display device to enable the movable link of the stereoscopic display device. Still preferably, the surgical microscope system is comprised of a subsidiary arm linked with the base and the stereoscopic display device to enable the movable link of the stereoscopic display device. More preferably, the stand is comprised of a parallel linkage including paired parallel first and second standing links and paired parallel upper and lower lying links, an intermediate portion of the first standing link being pivotally supported through a first pivot to a main body of the stand, the upper lying link having a joint shaft to pivotally link with the first standing link and being kept horizontal; a supporting link extended from the upper lying link; a tip link pivotally supported to the supporting link via a first tip link pivot at a distal end of the supporting link, the tip link supporting the microscope and the display device; a crank member pivotally supported by the joint shaft, the crank member having a first crank pivot and a second crank pivot so dimensioned as to have a line formed of the first crank pivot and the joint shaft kept horizontal and have a line formed of the second crank pivot and the joint shaft kept vertical; a standing sub-link pivoted on a second pivot formed on the main body and on the first crank pivot of the crank member, the standing sub-link having a length so as to have the first pivot, the first crank pivot, the second pivot and the joint shaft to form vertexes of a parallelogram; a lying sub-link pivoted on the second crank pivot and pivoted on a tip link pivot of the tip link, the lying sub-link having a length so as to have the joint shaft, the first tip link pivot, the second tip link pivot and the second crank pivot to form vertexes of a parallelogram; a counter weight provided below the parallel linkage mechanism to keep balance with a weight applied in a lowering direction of the parallel linkage mechanism about the first pivot whereby the free motion with keeping the particular orientation of the support relative to the movable base is enabled.

DETAILED DESCRIPTION OF THE EXEMPLARY EMBODIMENTS

Exemplary embodiments of the present invention will be described hereinafter with reference to FIGS. 1 to 8. Throughout the specification and claims, directions are defined and used to correspond to directions shown in FIGS. 1 and 2. Further, a relative term "distal" in regard to any member longer than is wide is defined and used as distal from a base 2 in its connection order from the base 2, and "proximal" is opposite thereto.

Figure 1:
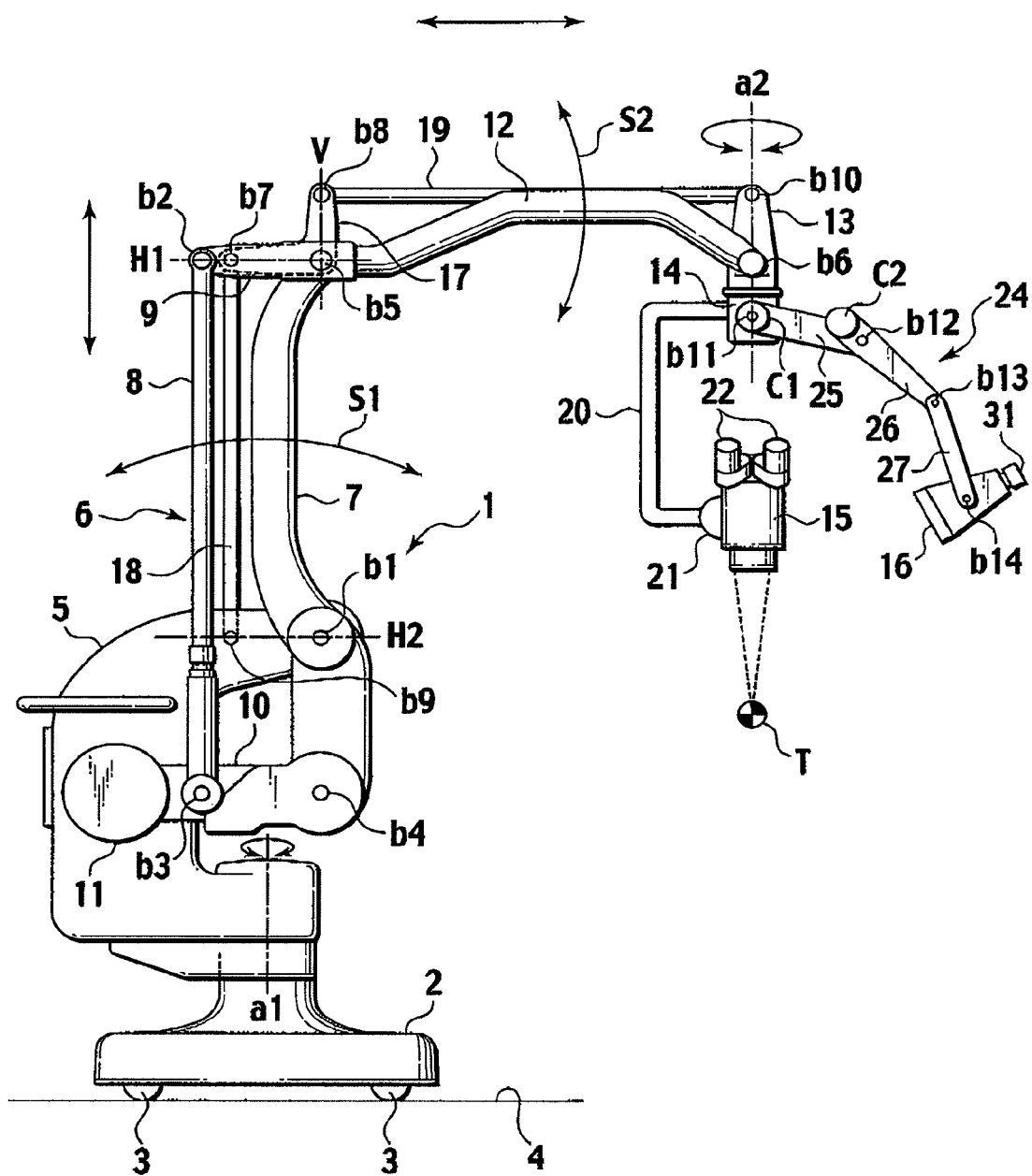
FIG. 1 is a side view of a surgical microscope system according to a first embodiment of the present invention.
Figure 2:
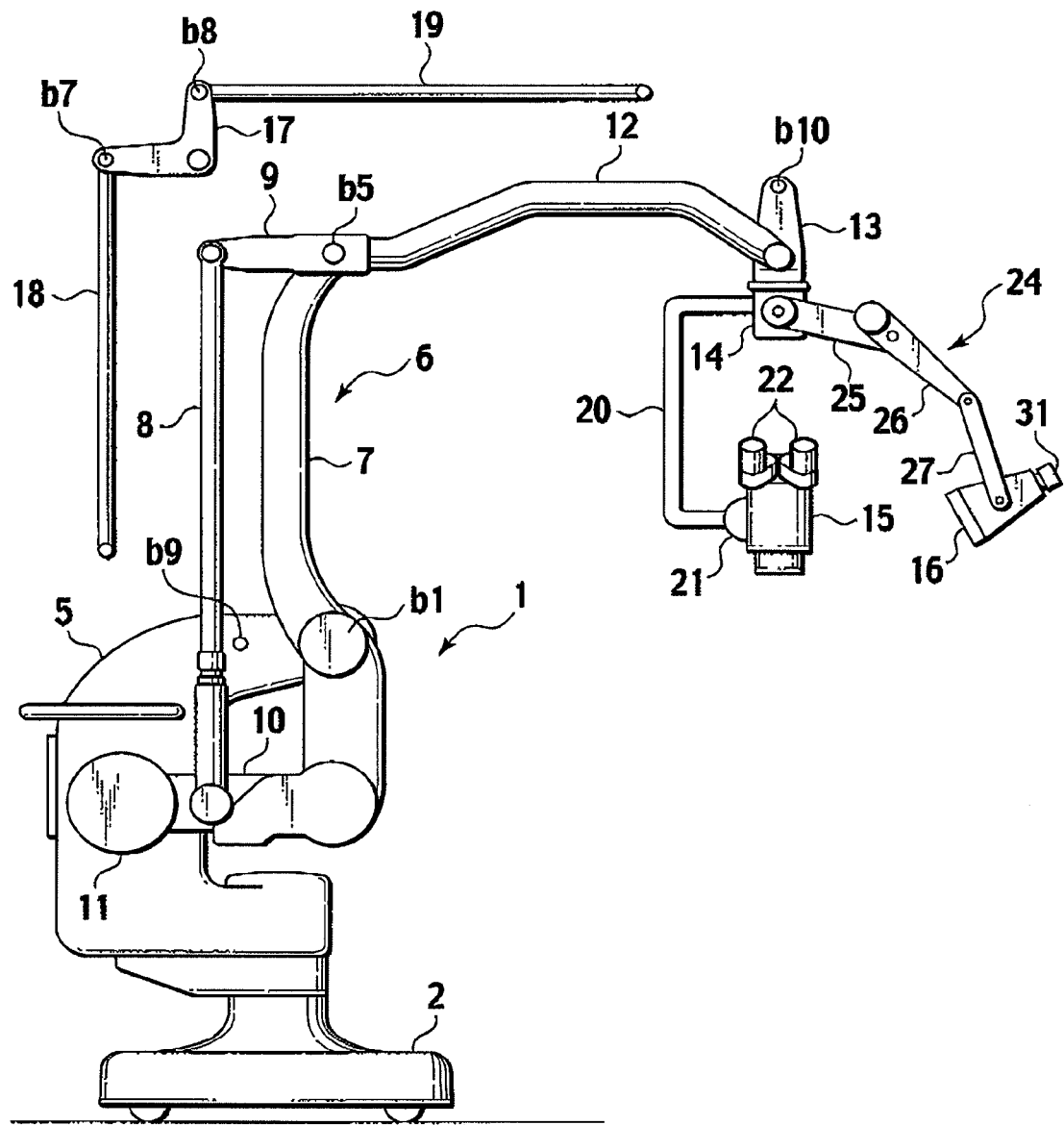
FIG. 2 is a partially exploded side view of the surgical microscope system.

Referring to FIGS. 1 and 2, a surgical microscope system is comprised of a stand 1, which is comprised of a base 2 and casters 3 for enabling the base 2 to move on a floor 4. A vertical pivot a1 is fixed to an upper face of the base 2 and a main body 5 having a C-letter-like shape is pivotally supported by the pivot a1. The pivot a1 is further comprised of a clutch system such as, but not limited to, an electromagnetic clutch so as to controllably free and lock rotation of the main body 5 about the pivot a1.

The main body 5 is comprised of a horizontal pivot b1 in the vicinity of a top thereof, which pivotally supports a parallel linkage mechanism 6. The parallel linkage mechanism 6 includes paired parallel standing links 7 and 8 and paired parallel lying links 9 and 10, which are mutually linked at respective ends via pivots b2, b3 and b4 and a joint shaft b5. A pivotal support of the parallel linkage mechanism 6 by the pivot b1 is made on a proper intermediate portion of the link 7 between both the pivot b4 and the joint shaft b5. The pivot b1 allows swinging motion S1 of the link 7 and is also comprised of a clutch system such as, but not limited to, an electromagnetic clutch so as to controllably free and lock the swinging motion of the link 7.

The standing link 7, in particular an upper part relative to the pivot b1, may be curved leftward to avoid interference with an operation to be carried out at the right side of the main body 5. An end of the lying link 10 at the lower side is linked with the link 7 via the pivot b4 and a counter end thereof is comprised of a counter weight 11 to keep balance with weights weighing on the parallel linkage mechanism 6.

The lying link 9 at the upper side is extended to form a supporting link 12 projecting rightward. A tip link 13 is pivotally supported by a pivot b6 at a distal end of the supporting link 12. The supporting link 12 is also curved upward so as to avoid interference with the operation to be carried out below the supporting link 12.

A lower end of the tip link 13 is comprised of a support box 14 formed in a box shape and made rotatable about a vertical axis a2. The support box 14 supports a stereoscopic surgical microscope 15 and a stereoscopic display device 16 as will be described later.

The parallel link mechanism 6 further includes a crank member 17 and sub-links 18 and 19. The crank member 17 is pivotally supported by the joint shaft b5 and has a substantially right-angled L-letter shape, which is comprised of a crank pivot b7 in the vicinity of an end of its horizontal portion and a crank pivot b8 in the vicinity of an upper end of its vertical portion.

The pivot b7 pivotally supports the standing sub-link 18. An opposite end of the sub-link 18 is pivoted on a pivot b9 formed on the main body 5. The sub-link 18 has the same length as a length between the pivot b1 and the joint shaft b7. More specifically, the sub-link 18, the standing link 7, the crank member 17 and the main body 5 are so formed as to have the pivots b1, b7 and b9 and the joint shaft b5, to form vertexes of a parallelogram. Thereby, even while the parallel linkage mechanism 6 swings, a line H1 passing both axes of the joint shaft b5 and the pivot b7 is steadily kept horizontal as a line H2 passing both axes of the pivots b1 and b9 is made to be horizontal. Moreover, a line V passing both axes of the joint shaft b5 and the pivot b8 is steadily kept vertical as the crank member (17) is formed in the right-angled L-letter shape.

Because of the aforementioned parallelism and the right-angularity of the crank member 17, a line V passing both axes of the pivots b8 and the joint shaft b5 is steadily kept vertical. The pivot b8 also pivotally supports the lying sub-link 19. An opposite end of the sub-link 19 is pivoted on a pivot b10 formed on the tip link 13. The sub-link 19 has the same length as a length between the pivot b6 and the joint shaft b7. More specifically, the sub-link 19, the lying supporting link 12, the crank member 17 and the tip link 13 are so formed as to have the joint shaft b5 and the pivots b6, b10 and b8 to form vertexes of a parallelogram. Thereby the axis a2, therefore the support box 14 as well, is steadily kept vertical even while the parallel linkage mechanism 6 swings. More specifically, the parallel linkage mechanism 6 allows the support box 14 to be capable of tree motion with keeping a particular orientation of verticality.

Figure 3:
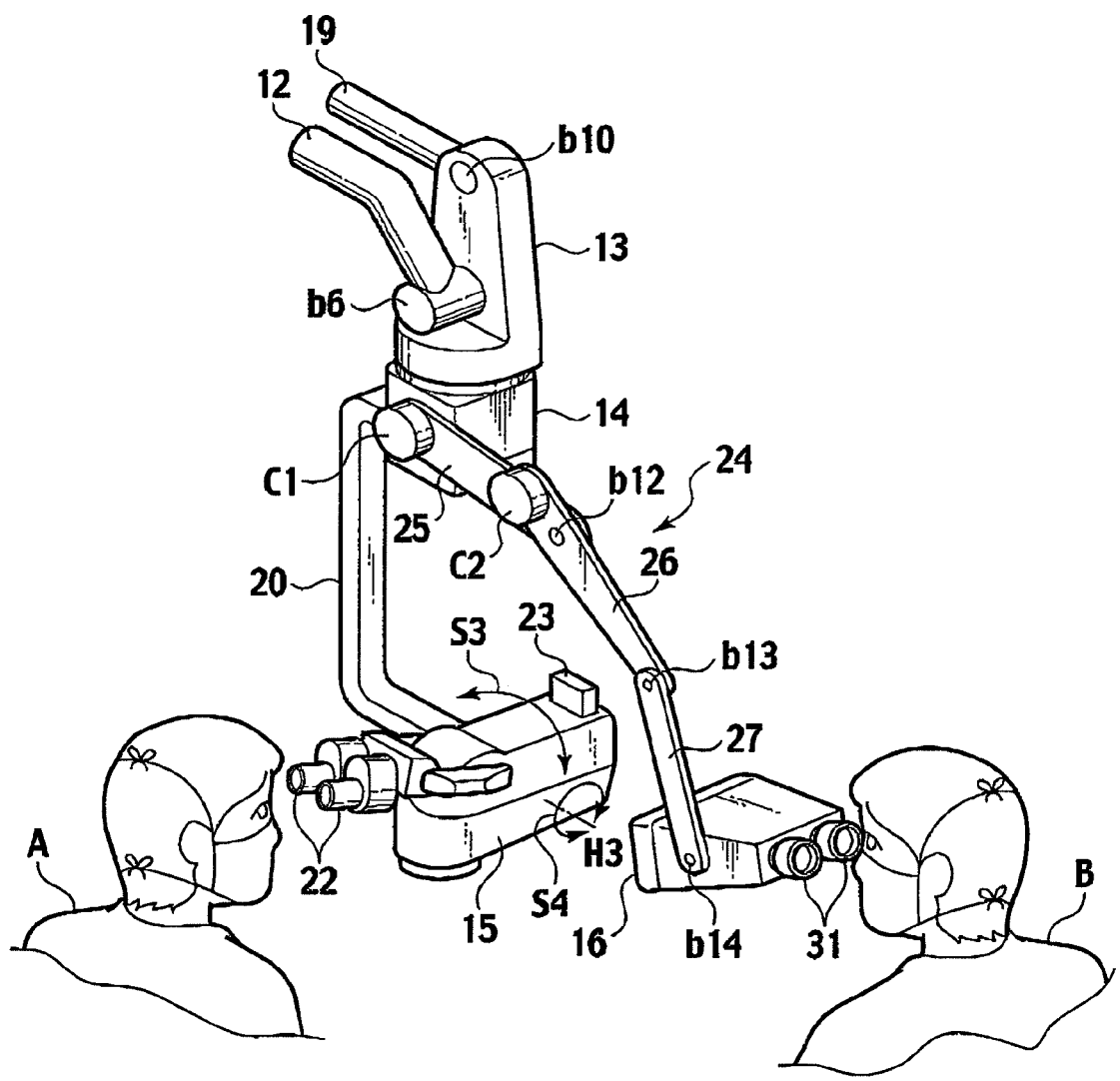
FIG. 3 is a perspective view of a stereoscopic surgical microscope, a stereoscopic display device and respective observing persons thereof.
Figure 4:
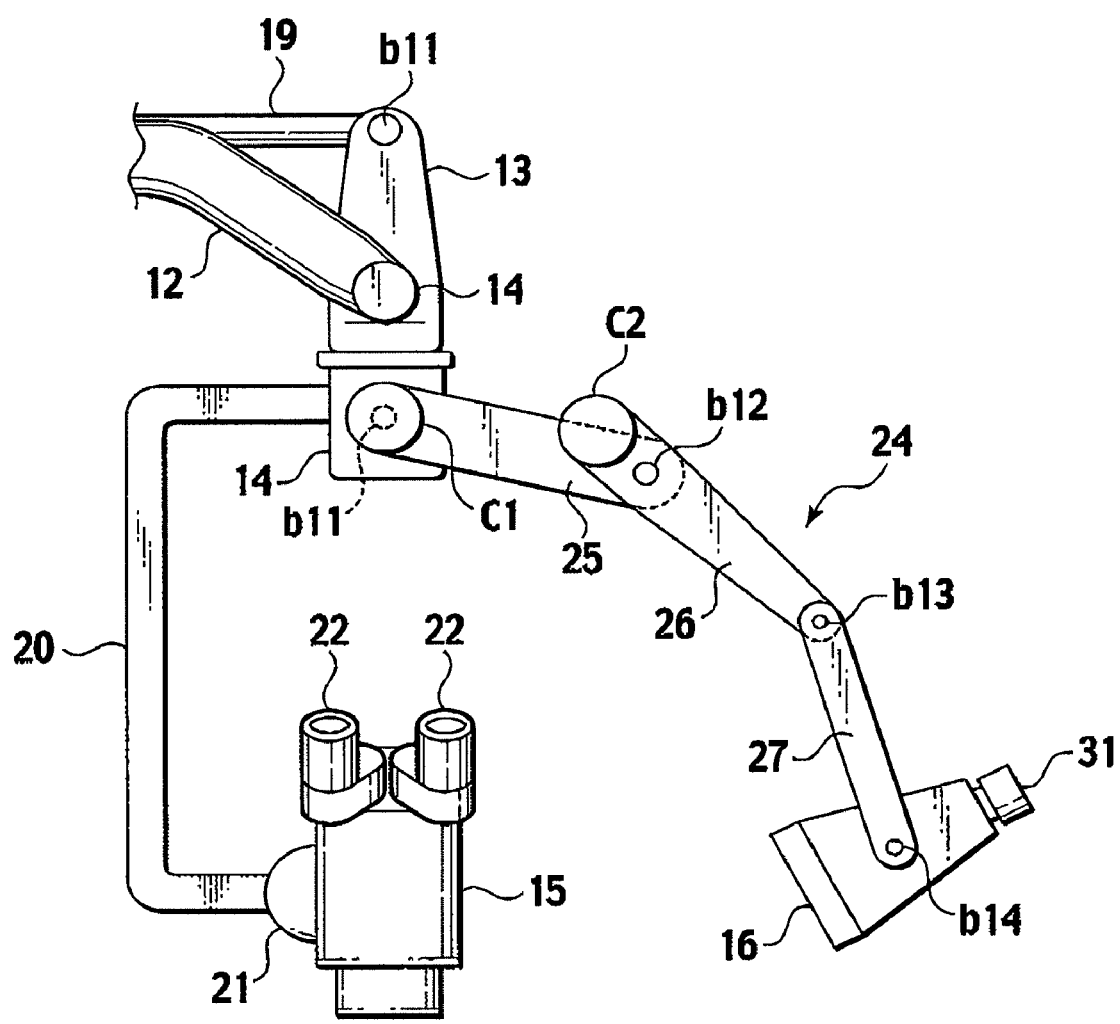
FIG. 4 is a side view of the stereoscopic surgical microscope and the stereoscopic display device.

Referring to FIGS. 3 and 4, the stereoscopic surgical microscope 15 is fixedly supported by the support box 14 kept vertical via an interposed hanging arm 20 formed to be a C-letter shape. A lower end of the hanging arm 20 is comprised of a joint 21 to allow the stereoscopic surgical microscope 15 to be in rolling motion S3 about a longitudinal axis and rocking motion S4 about a horizontal axis H3.

The stereoscopic surgical microscope 15 is comprised of a pair of optical systems, each having an object lens system, a zoom lens system and an eye lens system so as to magnify an objective body part. As the optical systems are provided in pair, the paired optical systems generate binocular parallax so that a surgeon A looking into eyepieces 22 is given a stereoscopic magnified view of the objective body part.

The stereoscopic surgical microscope 15 is further comprised of a camera 23 optically coupled with the paired optical systems thereof. As bundles of rays respectively introduced through the optical systems are partly branched and introduced into the camera 23, the camera 23 is capable of taking stereoscopic image. The camera 23 may be comprised of paired imagers so as to take right and left images independently, which consist the stereoscopic image. Color image sensors may be applied to the camera 23 so as to provide color images, however, alternatively or additionally, fluorescence sensors, spectroscopic image sensors or such analytic sensors may be applied to the camera 23. Such sensors provide different information from the visible ray views observable in the stereoscopic surgical microscope 15.

Figure 5:
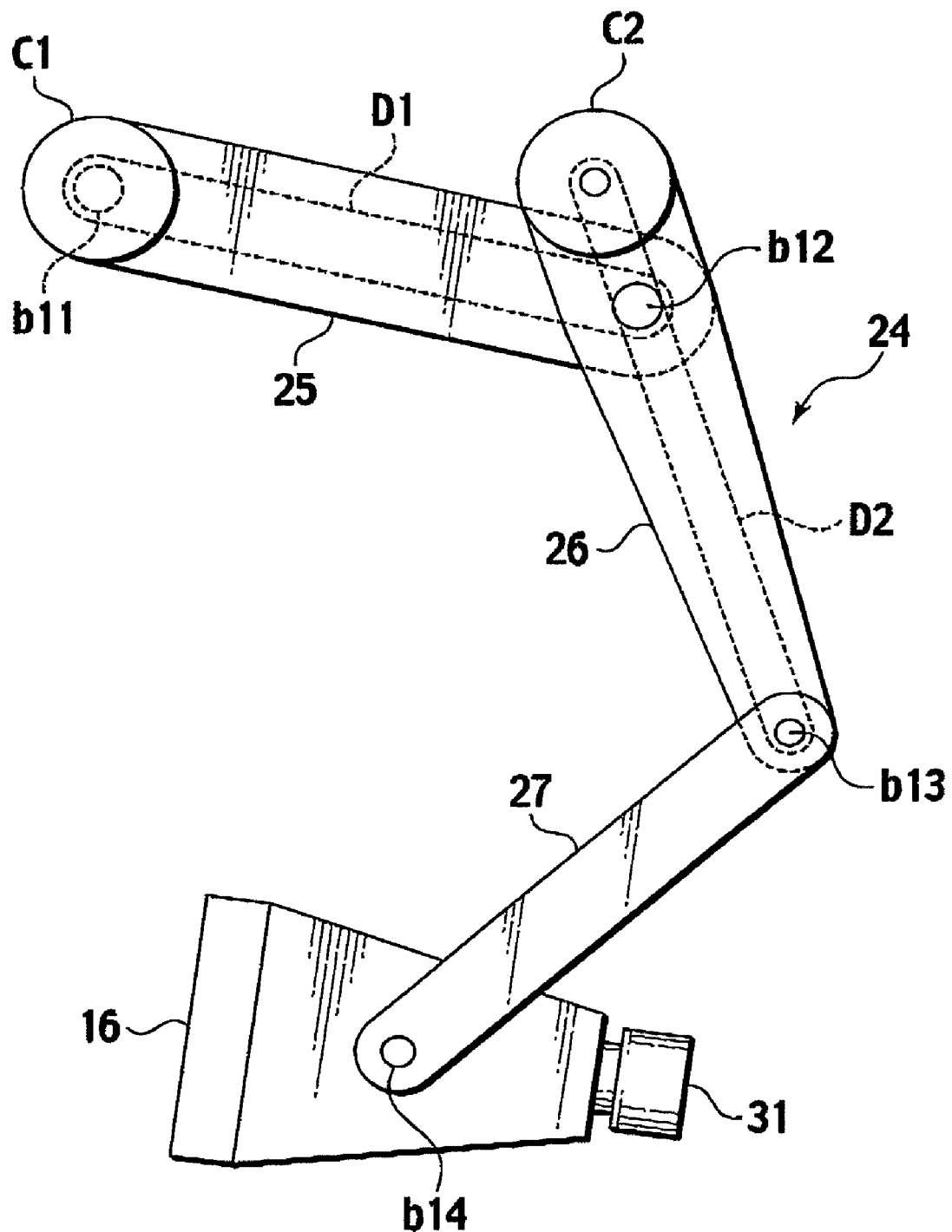
FIG. 5 is a side view of the stereoscopic display device and a subsidiary arm supporting the stereoscopic display device.

Referring to FIGS. 4 and 5, the stereoscopic display device 16 is movably supported by the support box 14 via a subsidiary arm 24. The subsidiary arm 24 is comprised of a first arm 25, a second arm 26, and a third arm 27.

A proximal end of the first arm 25 is swingably pivoted on a pivot bit formed on the support box 14. The pivot b11 is comprised of a clutch system such as, but not limited to, an electromagnetic clutch so as to controllably free and lock the swinging motion of the first arm 25.

The proximal end of the first arm 25 is further comprised of another clutch system C1 such as, but not limited to, an electromagnetic clutch. A distal end of the first arm 25 has a pivot b12 to pivotally support the vicinity of a proximal end of the second arm 26. As shown in FIG. 5, a timing belt D1 housed in the first arm 25 links the clutch system C1 with the pivot b12 so as to controllably free and lock the swinging motion of the second arm 26 about the pivot b12.

The proximal end of the second arm 26 is further comprised of another clutch system C2 such as, but not limited to, an electromagnetic clutch. A distal end of the second arm 26 has a pivot b13 to pivotally support the third arm 27. A timing belt D2 housed in the second arm 26 links the clutch system C2 with the pivot b13 so as to controllably free and lock the swinging motion of the third arm 27 about the pivot b13.

A distal end of the third arm 27 has a pivot b14 to pivotally support the stereoscopic display device 16. The stereoscopic display device 16 has such a movable link with the support so as to be movable independently of the stereoscopic surgical microscope 15. The pivot b14 is given proper friction, thereby the stereoscopic display device 16 is capable of swinging about the pivot b14 under the proper friction.

Figure 6:
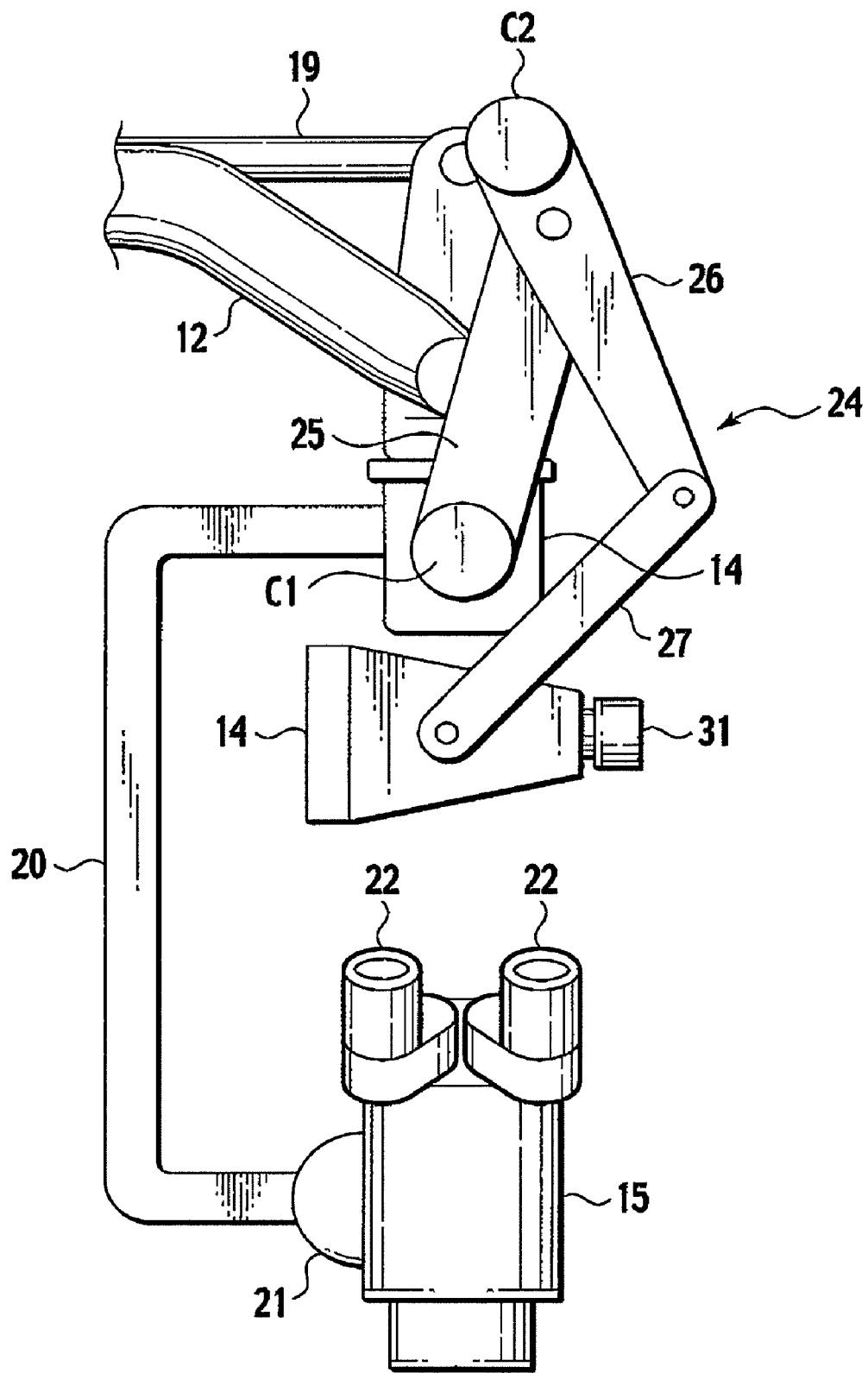
FIG. 6 is a side view of the stereoscopic display device and the subsidiary arm, which shows a state that the subsidiary arm is folded so as to retract the stereoscopic display device.

The clutch systems of the subsidiary arm 24 may be collectively controlled by a single switch or such (not shown). Then the subsidiary arm 24 may be folded so as to retract the stereoscopic display device 16 to a space between the support box 14 and the stereoscopic surgical microscope 15 as shown in FIG. 6.

Figure 7:
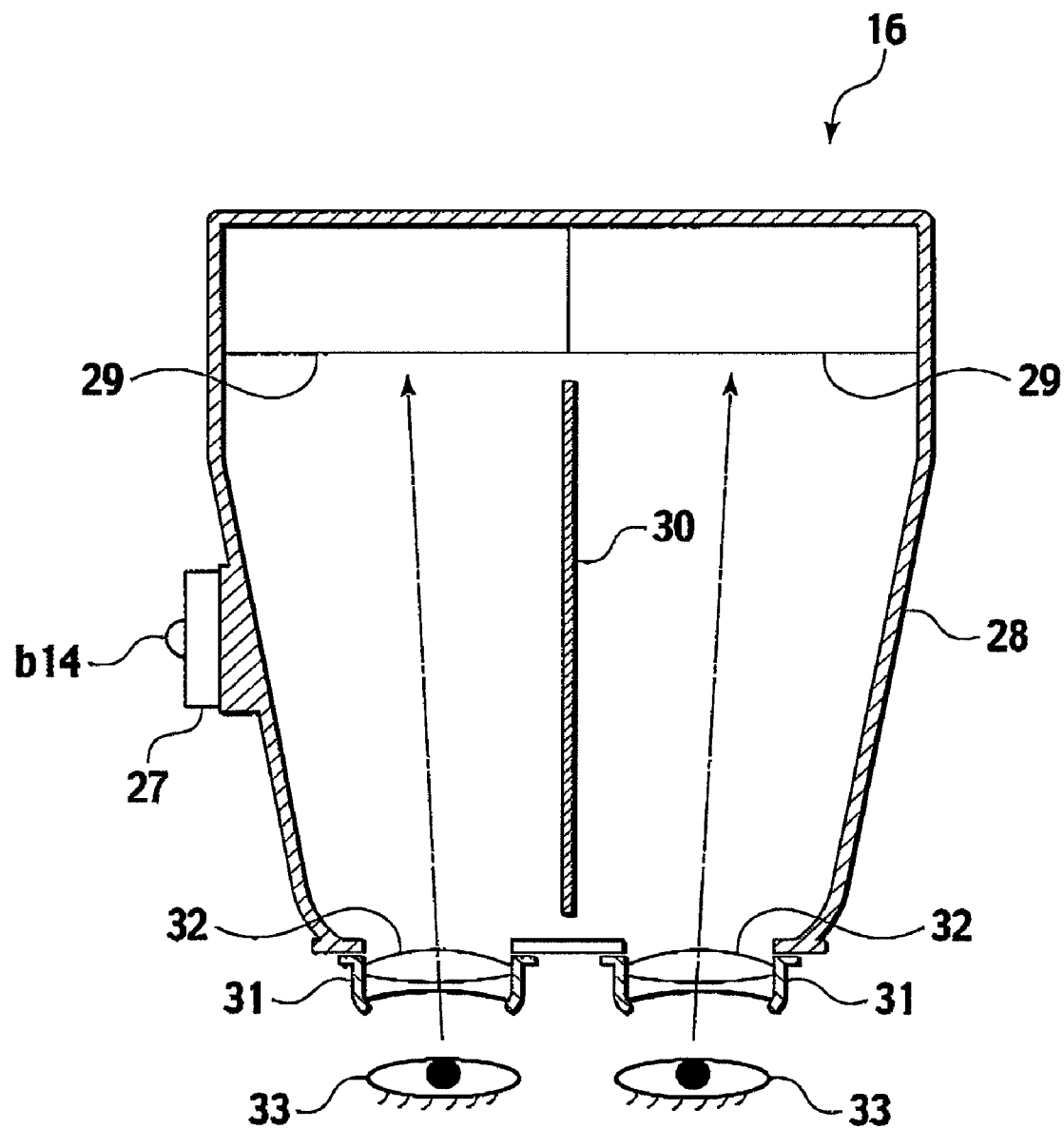
FIG. 7 is a sectional plan view of the stereoscopic display device.

Referring to FIG. 7, the stereoscopic display device 16 is comprised of a case 28, a display screen 29 housed in the case 28, and a partition 30 spatially partitioning the interior of the case 28. The display screen 29 is capable of projecting two independent images respectively on right and left halves thereof, or alternatively may be partitioned into right and left screens for respectively projecting right and left images.

The display screen 29 is electronically coupled with the camera 23 so as to project the right and left images respectively on the right and left halves. The case 28 is comprised of right and left optical systems, each of which has an eyepiece 31 and an object lens 32, for respectively showing the right and left images to the right and left eyes 33 of an assistant B so that the assistant B is given a stereoscopic magnified view of the objective body in common with the surgeon A. Although the coupling of the display screen 29 with the optical systems of the stereoscopic surgical microscope 15 is stated to be electronic in the above description, the coupling may be alternatively established by optical means or any other means.

Any information regarding the operation, such as vital signs or what are taken by CT, MRI and such, may be also superimposed on the images on the display screen 29.

Weights of the stereoscopic surgical microscope 15, the stereoscopic display device 16 and such weighing on one side of the parallel linkage mechanism 6 in total is balanced with the counter weight 11. Therefore, when the clutch systems of the stand 1 are all set to free the respective motions, one can move the stereoscopic surgical microscope 15 and the stereoscopic display device 16 merely with gentle force by hand. When he/she detaches the hand therefrom, the stereoscopic surgical microscope 15 stands still where it is moved, as the counter weight 11 keeps the balance. The balance is steadily kept without re-balancing even though the subsidiary arm 24 is folded or any other change occurs.

Figure 8:
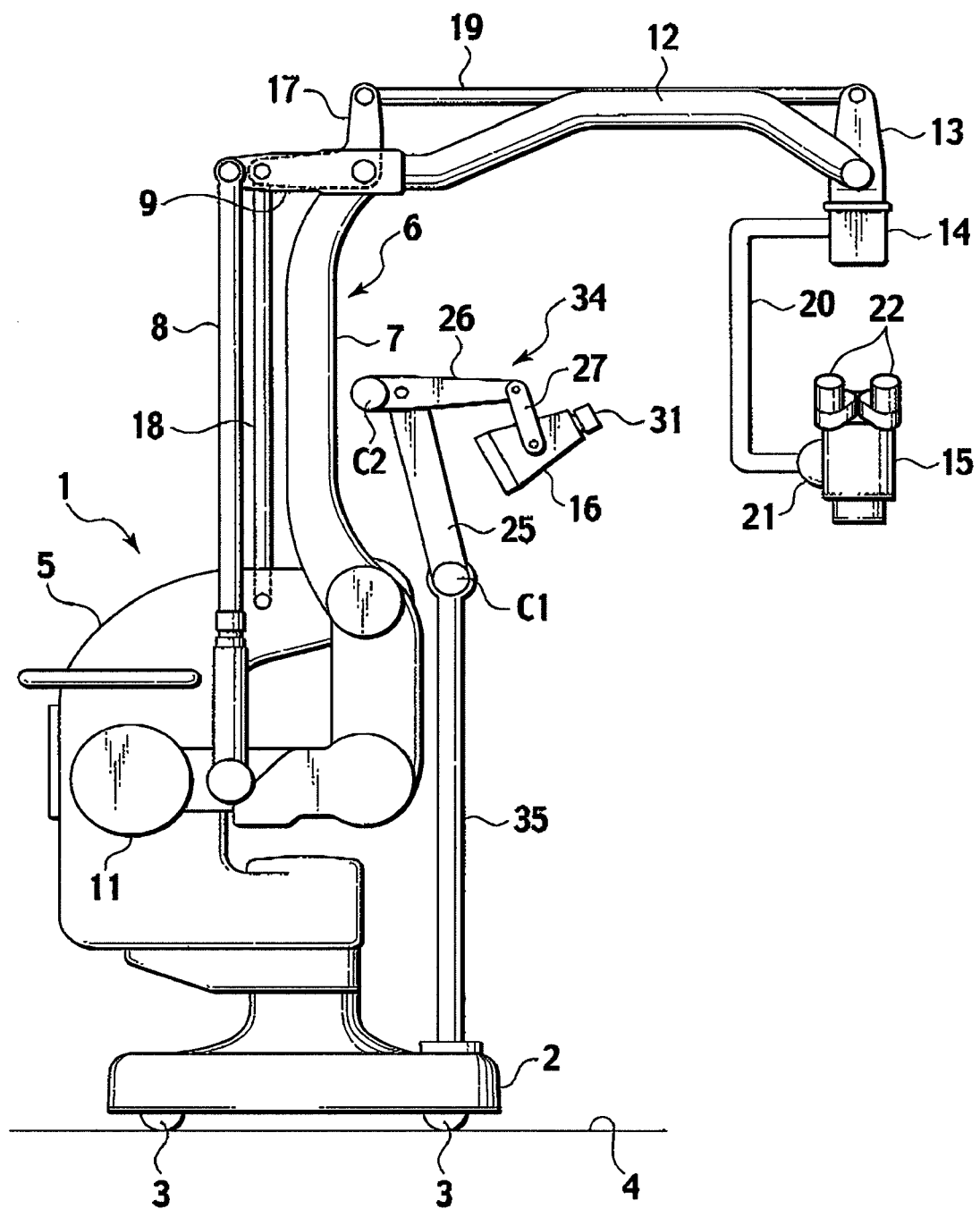
FIG. 8 is a side view of a surgical microscope system according to a second embodiment of the present invention.

The aforementioned first embodiment may be modified into a second embodiment as will be described hereinafter with reference to FIG. 8.

In accordance with the second embodiment, the stereoscopic display device 16 is supported directly by the base 2 of the stand 1 instead of being supported by the support box 14. A subsidiary arm 34 includes a stiff standing pole 35 securely fixed to the base 2 as well as the arms 25, 26 and 27 having substantially the same structure as those aforementioned. The distal end of the third arm 27 swingably supports the stereoscopic display device 16 in the same way as those of the first embodiment.

As the base 2 is the most stabilized member among members of the surgical microscope system, stability of views displayed by the stereoscopic display device 16 can be assured.

The stereoscopic display device 6 of the second embodiment serves views not only to the assistant B but also to the surgeon A as the stereoscopic display device 16 can be positioned just beside the stereoscopic surgical microscope 15 and is oriented toward the surgeon A. This structure provides another benefit to the surgeon A because the surgeon A can immediately check information displayed in the stereoscopic display device 16 particularly when it displays different information from the stereoscopic surgical microscope 15.

Further, the stereoscopic display device 16 may be supported by any member such as the main body 5 or any part of the parallel linkage mechanism 6 instead of the base 2 or the support box 14. In addition, another stereoscopic display device may be further provided on any member or apart from the stand 1 so as to distribute views to plural members.

The present invention will be enabled by any of or any combination of the aforementioned exemplary embodiments.

Although the invention has been described above by reference to a certain embodiment of the invention, the invention is not limited to the embodiments described above. Modifications and variations of the embodiment described above will occur to those skilled in the art, in light of the above teachings.

What is claimed is:

1. A surgical microscope system comprising:
   a stand including a movable base and a support capable of free motion with keeping a particular orientation relative to the base;
   a stereoscopic surgical microscope linked with the support, the microscope including a pair of first optical systems having a pair of eyepieces in direct optical contact with the microscope so as to provide a first stereoscopic magnified view;
   a stereoscopic display device including a display screen configured to display a stereoscopic image taken by the first optical systems and a pair of second optical systems so as to show the stereoscopic image as a second stereoscopic magnified view; and
   a subsidiary arm linked with the stand and the stereoscopic display device, the subsidiary arm enabling independent movement of the stereoscopic display device from the stereoscopic surgical microscope.

2. The surgical microscope system of claim 1, further comprising:
   a camera optically coupled with the first optical systems and electronically coupled with the display screen so as to project the stereoscopic image onto the display screen.

3. The surgical microscope system of claim 2, wherein the camera includes a pair of imagers respectively optically coupled with the first optical systems to take the stereoscopic image.

4. The surgical microscope system of claim 3, wherein the display screen includes a pair of separate screens respectively electronically coupled with the imagers.

5. The surgical microscope system of claim 1, wherein the subsidiary arm is linked with the support of the stand and the stereoscopic display device.

6. The surgical microscope system of claim 1, wherein the subsidiary arm is linked with the base of the stand and the stereoscopic display device.

7. The surgical microscope system of claim 5, wherein the stand includes;
   a parallel linkage including paired parallel first and second standing links and paired parallel upper and lower lying links, an intermediate portion of the first standing link being pivotally supported through a first pivot to a main body of the stand, the upper lying link having a joint shaft to pivotally link with the first standing link and being kept horizontal;
   a supporting link extended from the upper lying link;
   a tip link pivotally supported to the supporting link via a first tip link pivot at a distal end of the supporting link, the tip link supporting the microscope and the display device;
   a crank member pivotally supported by the joint shaft, the crank member having a first crank pivot and a second crank pivot so dimensioned as to have a line formed of the first crank pivot and the joint shaft kept horizontal and have a line formed of the second crank pivot and the joint shaft kept vertical;

a standing sub-link pivoted on a second pivot formed on the main body and on the first crank pivot of the crank member, the standing sub-link having a length so as to have the first pivot, the first crank pivot, the second pivot and the joint shaft to form vertexes of a parallelogram;

a lying sub-link pivoted on the second crank pivot and pivoted on a tip link pivot of the tip link, the lying sub-link having a length so as to have the joint shaft, the first tip link pivot, the second tip link pivot and the second crank pivot to form vertexes of a parallelogram;

a counter weight provided below the parallel linkage mechanism to keep balance with a weight applied in a lowering direction of the parallel linkage mechanism about the first pivot whereby the free motion with keeping the particular orientation of the support relative to the movable base is enabled.

8. The surgical microscope system of claim 1, wherein the subsidiary arm has a plurality of arms pivotally supported.

9. The surgical microscope system of claim 1, wherein the subsidiary arm has a clutch to free and lock a swinging motion of the arms.

* * * * *